(12) United States Patent
Vetter et al.

(10) Patent No.: US 7,828,777 B2
(45) Date of Patent: Nov. 9, 2010

(54) SEALING ELEMENT

(75) Inventors: Udo J. Vetter, Ravensburg (DE); Joachim Glocker, Weingarten (DE); Walter Schwarz, Bad Waldsee (DE)

(73) Assignee: Arzneimittel GmbH Apotheker Vetter & Co (DE)

( * ) Notice: Subject to any disclaimer, the term of this patent is extended or adjusted under 35 U.S.C. 154(b) by 671 days.

(21) Appl. No.: 10/479,206

(22) PCT Filed: May 18, 2002

(86) PCT No.: PCT/EP02/05505

§ 371 (c)(1),
(2), (4) Date: Mar. 1, 2004

(87) PCT Pub. No.: WO02/098470

PCT Pub. Date: Dec. 12, 2002

(65) Prior Publication Data

US 2004/0140285 A1     Jul. 22, 2004

(30) Foreign Application Priority Data

Jun. 1, 2001     (DE) .................... 101 27 779

(51) Int. Cl.
*A61M 5/32* (2006.01)
*A61B 19/00* (2006.01)

(52) U.S. Cl. .................... 604/192; 604/403

(58) Field of Classification Search .......... 604/87, 604/192, 411, 414, 415
See application file for complete search history.

(56) References Cited

U.S. PATENT DOCUMENTS

| 847,913 | A | | 3/1907 | Wilburn |
|---|---|---|---|---|
| 3,592,245 | A | * | 7/1971 | Schneller et al. ............. 141/25 |
| 3,715,047 | A | | 2/1973 | Sado |
| 3,986,508 | A | | 10/1976 | Barrington |
| 4,482,069 | A | | 11/1984 | Stadler |
| 5,158,550 | A | * | 10/1992 | Scholl, Jr. ................... 604/110 |
| 5,196,001 | A | * | 3/1993 | Kao ............................ 604/416 |
| 5,741,236 | A | * | 4/1998 | Kakiuti ....................... 604/192 |
| 5,833,653 | A | | 11/1998 | Vetter et al. |
| 5,891,129 | A | * | 4/1999 | Daubert et al. .............. 604/411 |
| 5,980,495 | A | | 11/1999 | Heinz et al. |
| 6,186,980 | B1 | * | 2/2001 | Brunel ........................ 604/110 |
| 6,187,265 | B1 | | 2/2001 | Wu et al. |

(Continued)

FOREIGN PATENT DOCUMENTS

CA     2299728 A1 *     9/2000

(Continued)

OTHER PUBLICATIONS

Office Action dated Jun. 24, 2008.

*Primary Examiner*—Melanie J Hand
(74) *Attorney, Agent, or Firm*—Bateman IP Law Group

(57) ABSTRACT

A sealing element is suggested, in particular one for closing primary packaging for medications, that has at least two parts, which touch each other at least in some areas. This is characterized in that steam-permeable channels are provided for sterilization of the contact surfaces. In addition, a method is suggested for manufacturing a syringe system with a sealing element. This is characterized by the steps—preliminary assembly of the sealing element, —sterilization of the sealing element, —final assembly of the sealing element.

25 Claims, 8 Drawing Sheets

U.S. PATENT DOCUMENTS 6,187,268 B1 2/2001 Albarella et al.
6,193,932 B1 2/2001 Wu et al.

FOREIGN PATENT DOCUMENTS

| CH | 397 953 | 2/1966 |
| DE | 196 38 940 | 4/1998 |
| DE | 198 58 418 | 6/1999 |
| DE | 198 58 391 | 7/1999 |
| EP | 0 085 360 | 1/1983 |
| EP | 0592814 | 4/1994 |
| GB | 847913 | 9/1960 |
| JP | 57-188262 | 11/1982 |
| JP | 07-033122 | 2/1995 |
| JP | 10-108908 | 4/1998 |
| JP | 10-305098 | 11/1998 |
| WO | WO 01/30421 A2 | 5/2001 |

\* cited by examiner

//TITLE// SEALING ELEMENT

BACKGROUND

1. Related Applications

The present application is the U.S. National Phase of PCT Application PCT/EP02/05505, filed May 18, 2002, claiming priority to German Patent Application No. 10127779.2, filed Jun. 1, 2001.

2. State of the Art

The invention relates to a sealing element according to the preamble of claim 1 and a method for producing a sealing element according to the preamble of claim 21.

Sealing elements and methods of the type addressed here are known. The sealing elements are used as sealing stoppers for primary packaging, as it is called, for medical purposes, especially for syringes and cannulas. It has been found that sealing elements of the type addressed here cannot be optimally sterilized in all cases: there are areas that cannot be reached directly by the sterilizing medium in a sterilizing method, e.g., during autoclaving, so that proper sterilizing cannot be ensured.

Therefore it is the object of the invention to provide a sealing element and a method for its production, which distinguish themselves in that an optimum sterilization is possible.

SUMMARY OF THE INVENTION

To achieve this object, a sealing element is suggested that comprises the characteristics named in claim 1. It is characterized in that channels are provided, through which the medium used for sterilizing, e.g., steam, can be brought to otherwise inaccessible locations, e.g., to contact surfaces on which parts of the closing element contact.

An embodiment of the sealing element is preferred that is characterized in that a first part is designed as a sterilization element. In this case, it is an element that is permeable by the sterilizing medium, which conducts this medium into areas that would otherwise be inaccessible for sterilization.

Another preferred embodiment example is characterized in that the sterilizing medium is guided into the inside of the sterilization element, i.e., that the channels run through this element. The sealing element is thus characterized by a simple structure.

Another preferred embodiment example is characterized in that the sterilization element is designed as a clamping element. In this way it is possible to optimally sterilize the sealing element and on the other hand, to ensure that with a simple structure a clamping of the sealing element, e.g., on a syringe body, is possible in a simple way.

Another preferred embodiment of the sealing element is distinguished in that the channels are used for guiding the sterilizing medium between two parts that comprise the sealing element. The parts are provided with projections and/or recesses in the contact area so that the sterilizing medium can be guided between the two parts, i.e., in the contact area.

An especially preferred embodiment of the sealing element is characterized in that the sterilization element forms a supporting element. It increases the mechanical strength of the sealing element in such a way that it can be used in connection with application aids, e.g., with motor-driven infusion and/or injection pumps without there being any malfunctions because the sealing element has elasticity that is too high.

Other advantages will be seen from the remaining subclaims.

To achieve the object of the invention, a method is also suggested for producing an injection system with a sealing element that has the characteristics named in claim 21 and is characterized in that the sealing element is preassembled first. This means, the parts of the sealing element are brought into the initial position, in which the later contact surfaces of the sealing element are still accessible to a sterilizing medium. In a next step, the sterilization is carried out. Finally, the parts of the sealing element are moved into their final positions in a final assembly step. The contact surfaces that are now formed are effectively cleaned in the preceding sterilization step, so that no contamination can result.

Especially preferred is an embodiment of the method that comprises the characteristics named in claim 26 and is characterized in that the sealing element is transferred to a syringe system by way of an autoclave of a filling device that is used as a sluice. Thus on one hand, the autoclave makes possible the sterilizing of the sealing element and on the other, is used to move sealing elements from a room that does not have aseptic conditions to another room that is subject to aseptic clean room connections.

Other embodiments of the method can be seen from the subclaims.

BRIEF DESCRIPTION OF THE DRAWINGS

The invention is described in more detail in the following using the drawings. They show.

DETAILED DESCRIPTION

Figure 1:
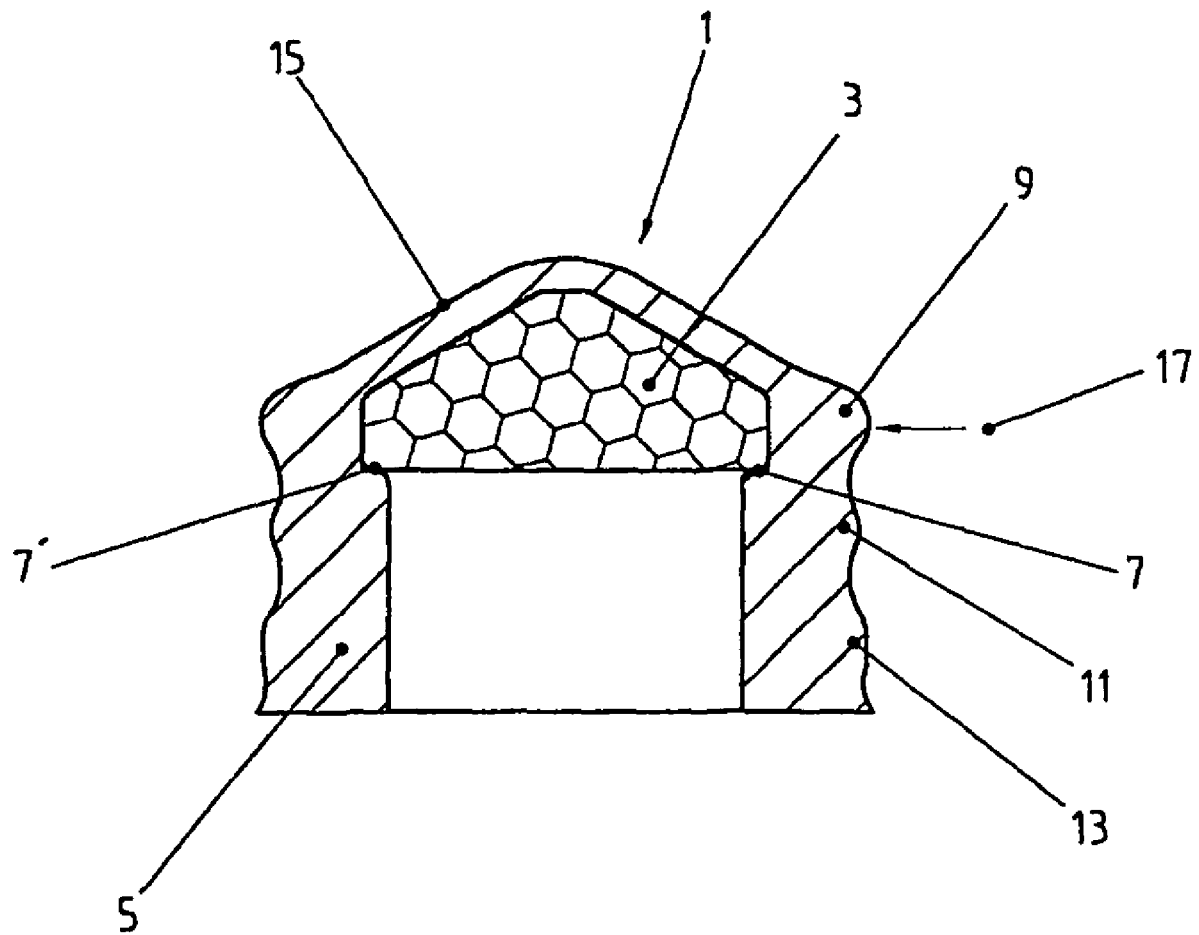
FIG. 1 shows a cross-section of a first embodiment example of a two-part sealing element.

FIG. 1 shows a sealing element 1 that consists of a support element 3 with a stable shape and an elastically deformable sealing sleeve 5. The support element 3 and the sealing sleeve 5 are designed as cylindrical rotation elements. The sealing sleeve 5 is designed in such a way that it is in contact with the majority of the surface of support element 3, i.e., at least partially surrounds it. The sealing sleeve 5 has, on the inside, a surrounding step 7, 7' that is also in contact with support element 3. Because of the elasticity of the sealing sleeve 5 and the step 7, into which the support element 3 can engage, the support element 3 is held securely.

Support element 3 is also characterized in that it has higher strength than the sealing sleeve 5. Thus it is used to stabilize the sealing element 1, in particular in the sense that the total elasticity of sealing element 1 is reduced, i.e., it is less compressible. Preferably the support element 3 is designed in such a way that it practically cannot be compressed.

With areas of its outer surface, support element 3 contacts the inside of sealing sleeve 5 so that these two parts form a common contact surface. In order to be able to sterilize the contact surface completely during a sterilizing procedure, it is provided that at least one of the parts of sealing element 1 has channels through which steam can pass, through which the sterilization medium can penetrate to the contact surface. For example, the support element 3 can be provided at least with channels permeable to steam. In the embodiment example shown here, the support element 3 is provided with structures that are permeable to steam, which are identified by honeycomb shading. In this case, it is preferable that the entire support element is provided with such a structure permeable to steam. Because of this, it can be ensured that when the sealing element 1 is exposed, steam can get through the entire support element 3 into the area of the contact surface with the sealing sleeve 5. This makes possible sterilization of all surfaces, i.e., even of the surfaces with which the support element 3 and the sealing sleeve 5 are in contact, in one work sequence.

The embodiment example shown is designed as a rotation element and is preferably used to seal a cylindrical tube that is not shown here, namely of a syringe body. The outside of sealing sleeve 5 has beads 9, 11, 13 around it. To seal the cylindrical tube, sealing element 1 is installed in it. In this way, the beads 9, 11, 13 come into contact with the inside surface of the cylindrical tube and in this process, form three surrounding sealing lips. In this way, sealing element 1 is installed in the cylindrical tube in such a way that its upper surface 15 forms a tightly closed interior space together with the inside wall of the tubes, i.e., of the syringe body, in which a fluid, especially a fluid medication and/or nutritional solution, etc. can be tightly enclosed in it. It can be seen that any excess pressure of the fluid that acts on the upper surface 15 of sealing sleeve 5 can be absorbed by the support element 3 lying behind it. In this way, an unintended deformation of sealing sleeve 5 is prevented because of the support effect of support element 3.

During a movement of the sealing element 1 in the inside of the tube and/or of a syringe body, a force is exerted on the side of support element 3 turned away from the surface 15 of sealing sleeve 5. Because of this, the sealing element 1 is displaced in the tube—upward in FIG. 1. It is clear that the thickness of the walls of sealing sleeve 5 is relatively small in the area of the upper surface 15, that forces exerted by a piston on the support element 3 are indirectly exerted on the fluid that is present in the closed chamber of the syringe. This means that during a displacement of sealing element 1, only a small deformation of sealing sleeve 5 can be caused due to the small wall thickness over the support element 3. Thus if a piston is slid into the inside of a syringe body by a specific movement path to move the sealing element 1, an amount of fluid that can be determined very precisely can be removed from the syringe. This is especially true if the elasticity of support element 3 is significantly lower than that of sealing sleeve 5.

On a sealing element 1 installed in a cylindrical tube, the inside diameter of which is slightly smaller than the outer diameter of the first bead 9, a sealing force develops between the first bead 9 and the inner cylinder wall that is indicated here by an arrow 17. It can be seen that this force required for the sealing effect is also absorbed by the support element 3 lying directly behind it. This means both the sealing force, as well as the forces caused by any excess pressure of the fluid to be sealed, are absorbed by support element 3. The beads 11, 13 are no longer stressed with sealing forces that are as high as the first bead 9; they are used to capture any leakage that may occur, which could develop at the first bead 9.

Support element 3 is thus arranged on the inside of sealing sleeve 5 in such a way that all significant forces that act on sealing sleeve 5 can be securely absorbed by support element 3. The sealing sleeve 5 can consist of a material that is optimum for the desired sealing of the inner chamber of the syringe body, but is also relatively soft. However, in the interaction with the stable support element 3, it acts like a significantly more rigid component and is thus effectively protected against undesired deformations by the forces acting on sealing sleeve 5.

Figure 2:
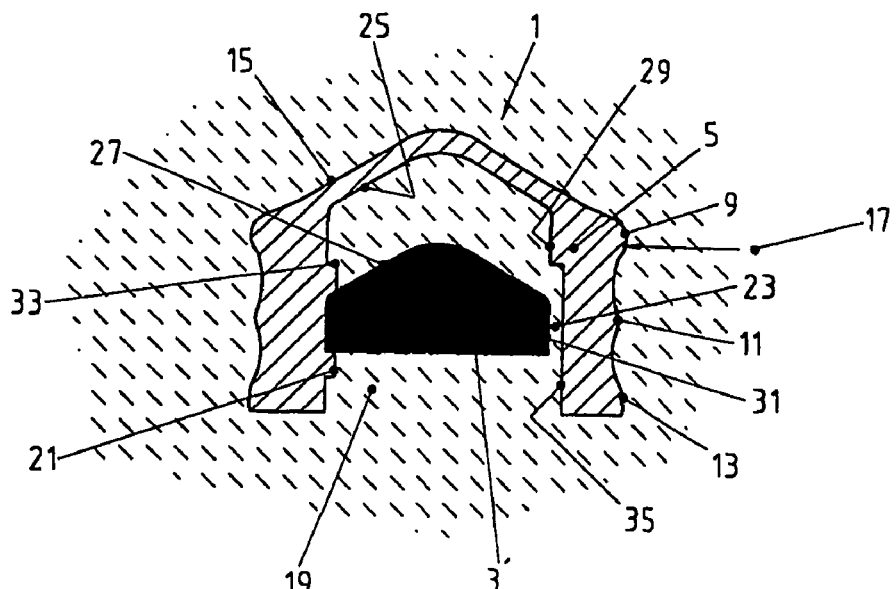
FIG. 2 shows a cross-section through a second embodiment example of a preassembled two-part sealing element.

FIG. 2 shows a second embodiment example of the sealing element, also designed as a rotation element. Common parts are provided with the same reference numbers so reference is also made to the description of FIG. 1.

The important difference from the preceding embodiment lies in that support element 3' does not have any steam-permeable structures. Support element 3' is shown in a first pre-assembly position. Sealing sleeve 5 has a recess 19 that is essentially cylindrical, the diameter of which is greater than that of the outer diameter of support element 3'. The inside surface 35 of recess 19 has at least two, preferably three, ribs of which rib 21 can be seen in cross-section here. The ribs surround an imaginary inner circle, the inner diameter of which corresponds approximately to the outer diameter of support element 3'. In this way, the ribs can form a holding device: they contact the outer surface of support element 3' with a certain prestress in such a way that it is securely held in the first preassembly position. The ribs hold support element 3' at a distance from inner surface 35 of sealing sleeve 5. Since in this way, the recess 19 on the inside of sealing sleeve 5 has an inner diameter that is larger than the outer diameter of support element 3, a slot 23 is formed that runs in the direction of ribs 21, which separates the ribs from each other in longitudinal direction. These slots thus form channels through which a sterilizing medium can go past the sides of support element 3' into the chamber inside the sealing sleeve 5, which is arranged above support element 3'. Because of this, the entire recess 19 of sealing sleeve 5 and the complete outer surface of support element 3' can be sterilized. So, for example, if hot steam is used for sterilizing, which is indicated here by shading, all the inner and outer surfaces of the sealing sleeve 5 and all surfaces of support element 3' can be reached and thus sterilized.

It can also be seen from FIG. 2 that the recess 19 is limited at the top by a contact surface 25, whose contour is adapted to the upper contour and thus the contact surface 27 of support element 3'. In the upper range of recess 19, there is a surrounding contact surface 29 that cooperates with a surrounding contact surface 31 of support element 3' when this is moved from the preassembly position shown in FIG. 2 into its later final assembly position, which will be discussed in more detail below. In addition, it can be seen in FIG. 2 that the upper end 33 of rib 21, which is shown in cross-section here, forms a latching device that holds support element 3' sealed in a locked manner when it is moved into its final assembly position.

Figure 3:
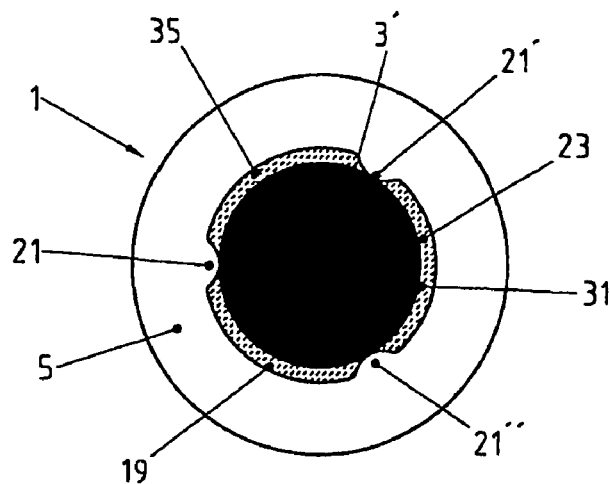
FIG. 3 shows a top view on the open side of the sealing element shown in FIG. 2.

FIG. 3 shows a bottom view in recess 19 of the sealing element 1 shown in FIG. 2. The sealing sleeve 5 and the recess 19 with ribs 21, 21', 21" can be seen. These are in contact with support element 3', which is thereby securely held in the first preassembly position. In addition, the surrounding slot 23 that is only interrupted by ribs 21, 21', 21" can also be seen, which is shown here as a dotted line. Because of the slot 23 that is formed by the surrounding contact surface 31 of support element 3' and the inside surface 35 of the sealing sleeve 5, hot steam provided for sterilizing can flow through. In this way, it is ensured that the entire sealing element can be autoclaved, i.e., sterilized, in the preassembled condition. The holding force on ribs 21, 21', 21" necessary for securely holding the support element 3' is applied by the inherent elasticity of the sealing sleeve 5'.

Figure 4:
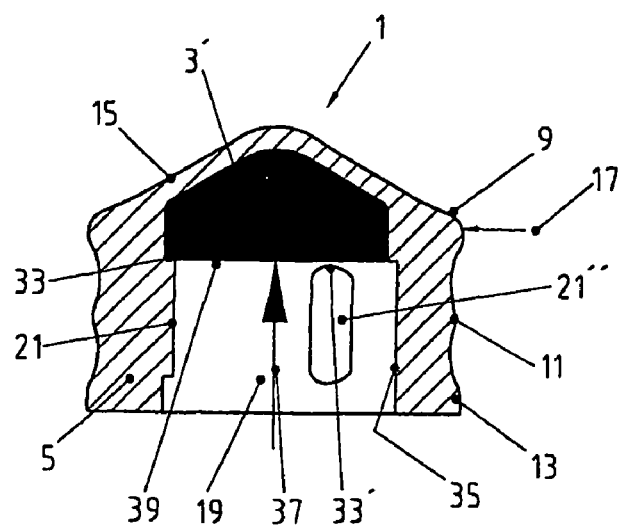
FIG. 4 shows a cross-section through the sealing element shown in FIG. 2 in assembled condition.

FIG. 4 shows the same view as FIG. 2 again with the difference that support element 3' is located in a second final assembly position. Common parts are provided with the same reference numbers, so reference is made to the description of the preceding figures. What can be seen is that the contact surfaces 25 to 31 explained in FIG. 2 are now in contact with each other. Arrow 37 indicates that the support element 3' is slid, by means of a suitable device, far enough in the direction of arrow 37 until it engages in the final position. How the support element 3' engages at the upper ends 33 and 33' of ribs 21, 21', 21" can be recognized. Support element 3' is thereby held securely against the contact surfaces 25 to 31 by residual forces, adhesion forces and frictional forces. The forces necessary for the friction are applied, in particular, by the inherent elasticity of sealing sleeve 5.

In assembled and installed condition, sealing element 1 can be slid along arrow 37 in a syringe body in a known way by means of a piston, which exerts forces acting on the support element 3' in the direction of arrow 37. Because of this, a fluid located in a cylindrical tube is exposed to overpressure that can be utilized for metered emptying of the cylindrical tube. In particular, this involves syringes or cannulas for injection of fluid medications and/or nutritional solutions, etc. In this process, a precise metering of the injection quantity is especially important, above all in automatic injection devices. In this process, precise metering is carried out by selective sliding of sealing element 1 in the direction of arrow 37. The force necessary for sliding the sealing element 1 thereby acts advantageously on the lower surface 39 of support element 3' in the direction of arrow 37. This force is transferred directly by way of the support element 3', over the upper contact surfaces 25 and 27 onto the sealing sleeve 5. It is also clear from this that, because of the transmission of force over a large surface and the forming effect of support element 3', an undesired deformation of the sealing sleeve 5 is practically precluded. This means that, by a sliding of the sealing element 1 by means of a force in the direction of arrow 37 a cylindrical tube that has a second opening, especially a syringe or cannula, can be emptied with precise metering, especially for medical injection of fluid medications and/or nutritional solutions, etc.

FIG. 4 shows that any forces of a fluid enclosed in a tube and/or in a syringe body on the upper surface 15 of sealing sleeve 5 and sealing forces that occur that are indicated by arrow 17, can be absorbed by support element 3' arranged on the inside of sealing element 1.

The embodiments of the sealing element 1 shown here as rotation elements are in no way binding. This means that the principle of an elastic sealing sleeve with a support element can be implemented in any type of tube and/or syringe body, e.g., in oval, polygonal tubes and also in tubes with optionally selected cross-section surfaces.

Figure 5:
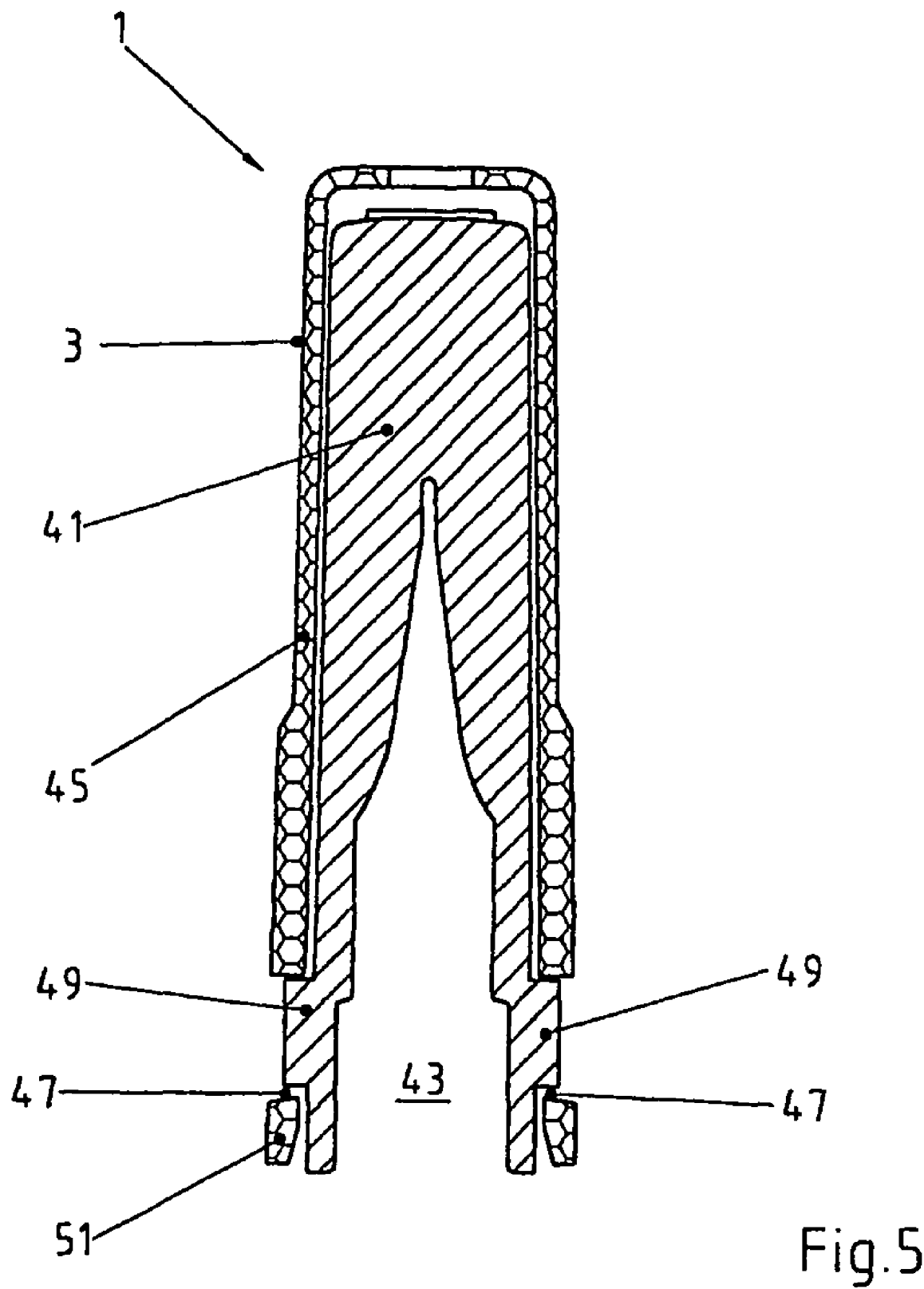
FIG. 5 shows a cross-section of another embodiment example with outer support elements.

FIG. 5 shows another embodiment example of a sealing element 1 that comprises two parts, namely a sealing cap 41 that is designed so that it is hollow in its lower area in FIG. 5 and comprises an inner chamber 43 into which the tip of a syringe can be introduced, together with an injection needle. This can be inserted into the base element of the sealing cap 41 when the sealing element 1 is placed on the syringe that is not shown here.

Sealing cap 41 is surrounded by a safety cap 45 that can be slipped over sealing cap 41. In the lower area of sealing cap 41, i.e., in the area of inner chamber 43, safety cap 45 is provided with recesses 47 that extend into the projections 49 of sealing cap 41. The recesses 47 are thus used as sight glasses.

Safety cap 45 continues downward into a ring 51, which surrounds the lower edge of sealing cap 41 and engages under projections 49 in such a way that when tensile forces are exercised on the safety cap 45, the sealing cap 41 of the sealing element 1 is pulled off the syringe.

Safety cap 45 stabilizes sealing cap 41 and thus is used as a support element 3' of the sealing element 1. Sealing cap 41 fills the inner chamber of safety cap 45 practically completely. Contact surfaces thus result between the inner surface of safety cap 45 and the outer surface of sealing cap 41. In order to ensure that the contamination present in the area of the contact surface can be deactivated, safety cap 45 is provided at least with channels that penetrate the walls of safety cap 45 and lead to the area of the contact surface. Preferably, the safety cap 45 is completely manufactured of a porous material that corresponds to that of the support element, which was described using FIGS. 1 to 4. For example, in this case, a sinter-like material can be used to manufacture the support element. If sealing element 1 that is shown in FIG. 5 is brought into a sterilizing medium, e.g., exposed to hot steam, this medium can securely reach the outer surface of the safety cap 45, the inner chamber 43 of the sealing cap 41, and also the contact surface between the two parts, since the material of safety cap 45 is permeable to steam, i.e., permeable to the sterilizing medium. It is also conceivable to manufacture sealing cap 41 with channels, porous structures or completely of porous material in order to be able to carry out a sterilization in the contact area and/or in the area of the contact surface. However, in the embodiment example shown in FIG. 5, channels can also lead into the area of the contact surface, as was explained with reference to FIGS. 2 and 3 in order to be able to carry out a sterilization.

Figure 6:
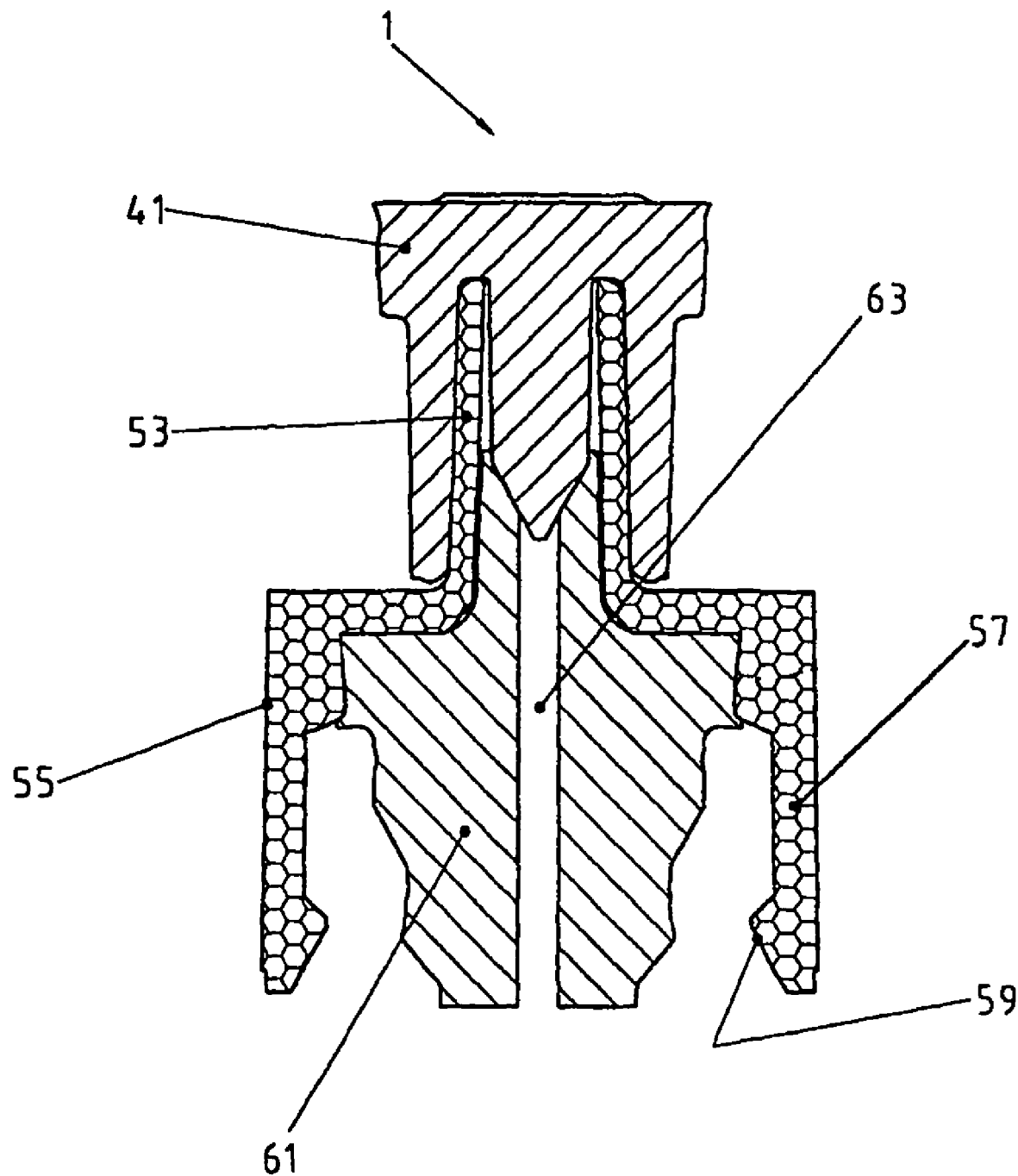
FIG. 6 shows a cross-section through a three-part sealing element with a coupling system and a device for fluid guiding.

The cross-section diagram according to FIG. 6 shows another embodiment example of a sealing element 1 that comprises a sealing cap 41. This is mounted on a conical projection 53 of a clamping element 55, on which if necessary an injection needle can also be mounted. The clamping element 55 has a cylindrical shroud 57 that engages the end area of a cylindrical tube and/or a syringe body, but this is not shown here. In the lower end area of shroud 57 turned away from sealing cap 41, projections serving as hooks 59 are provided on the inside of the shroud, which on the outside engage with the tube and/or syringe body in a locking manner in order to securely anchor the clamping element 55 on the tube and/or syringe body. On the inside of clamping element 55, a sealing stopper 61 is provided that closes and seals the end area of the tube and/or the syringe body and extends into the conical projection 53. Sealing stopper 61 has a central channel 63 that is tightly closed by sealing cap 41.

The cross-section diagram according to FIG. 6 shows that the parts of sealing element 1, in this case the sealing cap 41 and the sealing stopper 61 do not engage with each other directly, i.e., do not contact each other directly. The clamping element 55, which can have channels or porous structures, is found in the contact area between the two parts. It is provided here that the entire clamping element 55 consists of a porous, possibly sinter-like material. In this way it is possible to reach the otherwise inaccessible area between the parts of the sealing element 1 in an autoclaving and/or sterilizing process and deactivate contamination. Clamping element 55 thus acts as a sterilization element. It makes possible the entry of the sterilizing medium into the area in which the sealing cap 41 contacts the clamping element 55 and the clamping element 55 contacts sealing stopper 61. Since the sterilizing medium can access sealing element 1 from the inside and from the outside, it can be sterilized completely.

Figure 7:
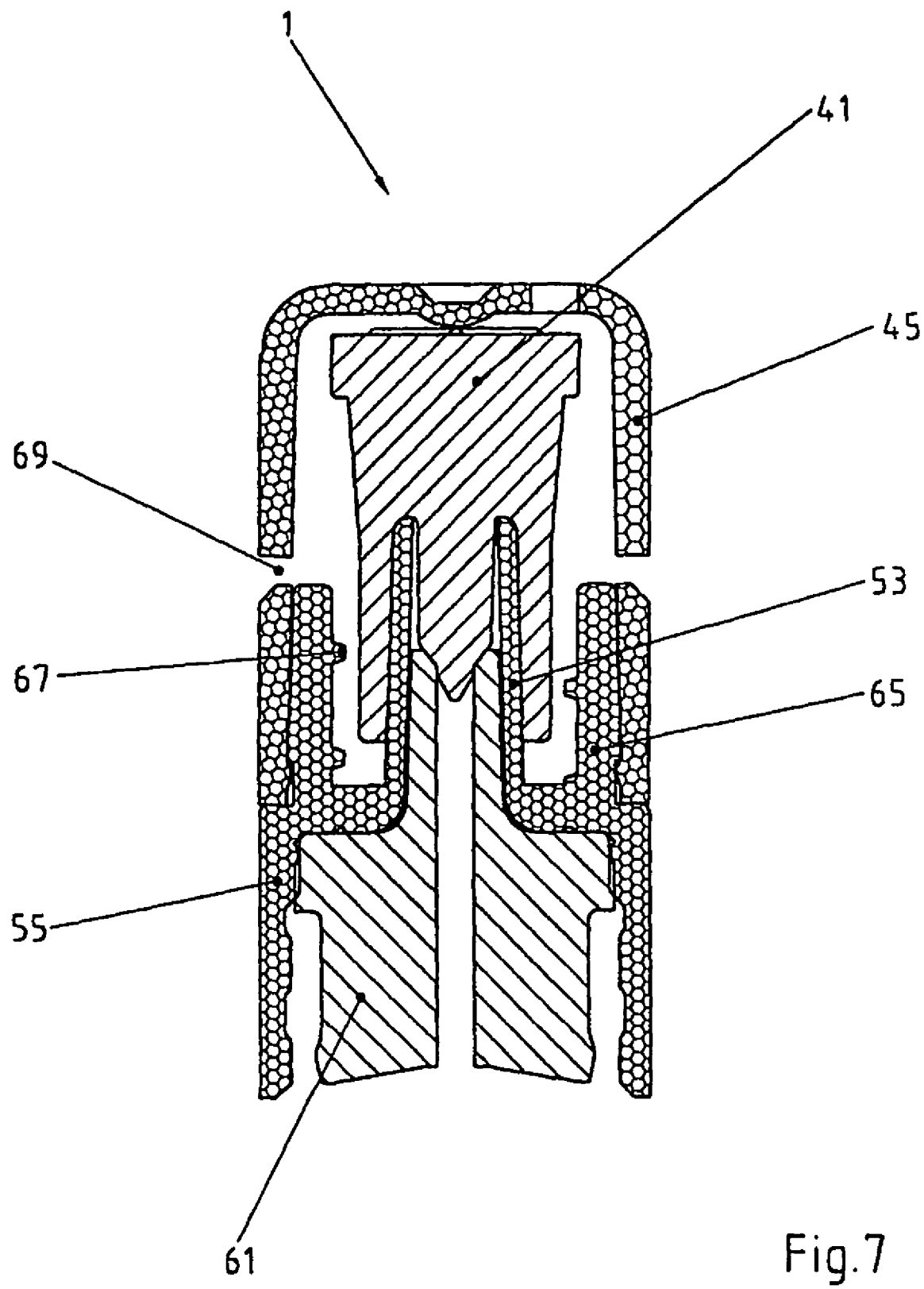
FIG. 7 shows a cross-section through another embodiment example of a sealing element with a safety cap.

The embodiment example of a sealing element 1 shown in FIG. 7 is basically set up as was shown in FIG. 6: it comprises a sealing cap 41 (a sealing member), a clamping element 55 serving as the sterilization element/member and a sealing stopper 61 (a sealing member) which, as in the embodiment example according to FIG. 6, is mounted on the inside of clamping element 55 and is used to seal a tube and/or a syringe body on which the clamping element 55 is mounted in the end area. Because of the clamping element 55 lying between sealing cap 41 and sealing stopper 61, which here consists e.g., completely of porous material, a sterilization of the area enclosed by the two sealing elements is thus possible. The clamping element 55 has a cylindrical projection 65 surrounding the conical projection 53, which can be provided with an internal thread 67 on its inside. This is used to securely hold a cannula mounted on the conical projection 53 and anchor it on clamping element 55.

In addition, a safety cap 45 (a porous sterilization member) is also provided here that engages over the sealing cap 41 and ensures that it cannot be damaged or unintentionally removed from the sealing element 1 assembly. Safety cap 45 surrounds the cylindrical projection 65 and is anchored on it so that it locks. A designated breaking point 69 is indicated by a gap: if a force is exerted on safety cap 45, the upper part of same will be broken off so that the sealing cap 41 is accessible and removable. A user can thus see, with no problem, whether any non-permitted manipulations have been carried out on sealing element 1. The safety cap 45 thus represents a so-called original seal or a guaranteed seal.

In the embodiment example shown here, safety cap 45 is provided with channels or with porous structures in order to be able to reach the outer surface of sealing cap 41 in a sterilizing procedure. It is also conceivable to manufacture the entire safety cap 45 of a porous material as shown in FIG. 7.

From the explanation of FIG. 7, it is clear that in the embodiment example shown here, as in the embodiment example according to FIG. 6, the clamping element 55 serves as a sterilization element/member, but also to stabilize the sealing element 1 itself. The fact that the clamping element 55 ultimately also serves as a support element of sealing element 1 is thus achieved.

Figure 8:
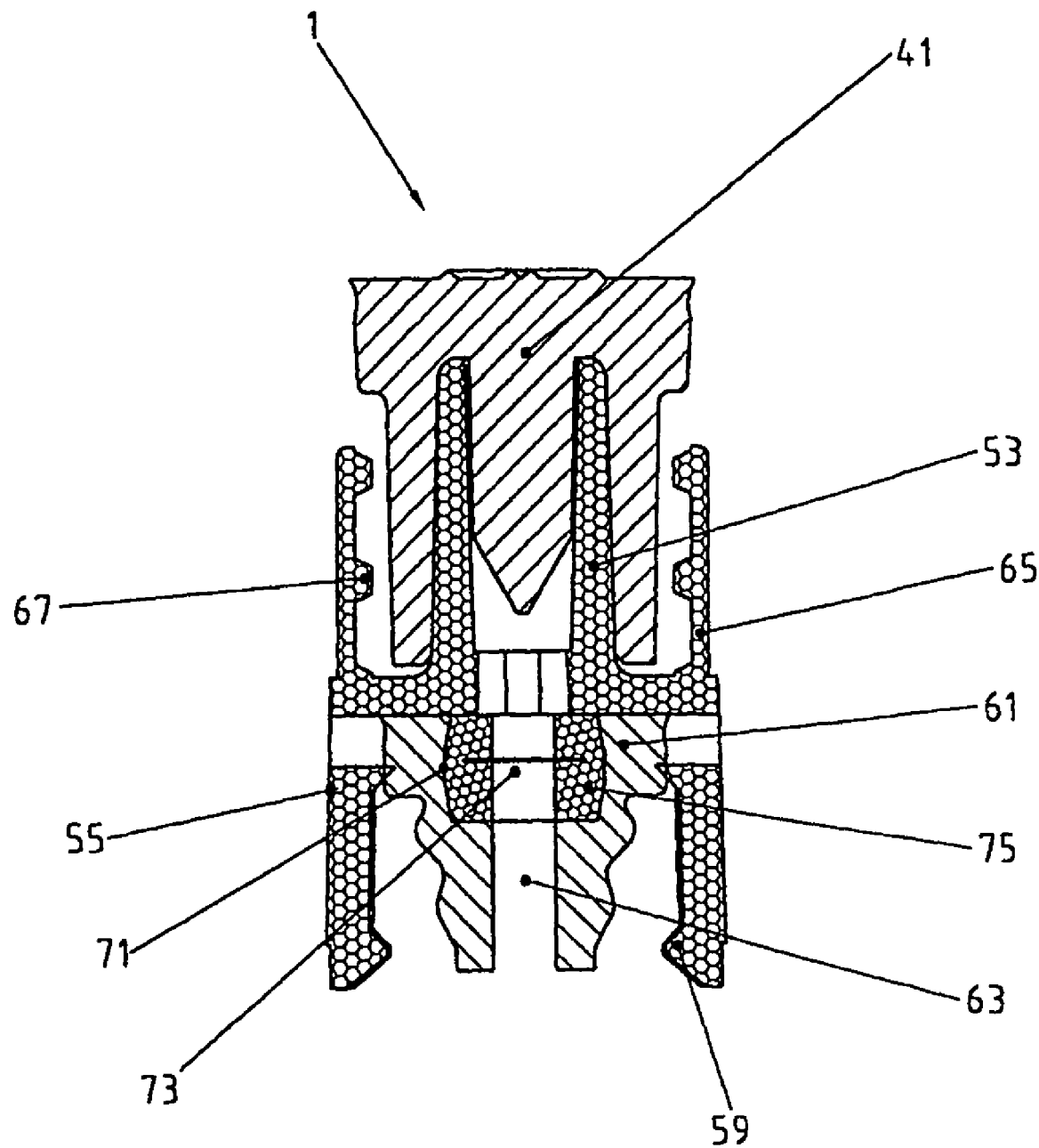
FIG. 8 shows a cross-section through another embodiment example of a sealing element with a filtering device.

FIG. 8 shows a further embodiment example of a sealing element 1 that essentially corresponds to the one that was explained in FIG. 7. Common parts are thus provided with the same reference numbers. However, in the illustration according to FIG. 8, the safety cap 45 is not mounted. In contrast to the embodiment examples previously described, in the area of the passage channel 63 of sealing stopper 61, a filter device 71 is provided that has a filter 73, fastened by a bracket 75, in the flow path of the medium that comes out of the tube and/or the syringe body. In this case bracket 75 is formed by a ring, which itself consists of porous material so that its contact surfaces against sealing stopper 61 can be sterilized. The ring of bracket 75 is shown here as a separate element. However, it is also possible for the bracket 75 to be a part of clamping element 55. The ring extends far enough into sealing stopper 61 so that it serves as a support element for sealing stopper 61 and ensures that the sealing stopper is pressed against the tube and/or a syringe body so that it seals when the sealing element 1 is mounted.

Purely by way of example, the embodiment shown in FIG. 8 is provided with a cylindrical projection 65 that surrounds the conical projection 53 and is provided with an internal thread 67.

FIG. 8 also shows that the clamping element 55 that serves as a sterilization element extends into the inside of sealing cap 41 in such a way that the cap is stabilized. The clamping element also acts as a support element here.

FIGS. 9 and 10 again show embodiment examples of sealing elements, but show the upper part of a syringe body 77 that has a conical projection 53', on which a cannula can be mounted. In the embodiment examples shown in FIG. 9, the sealing element 1 is designed similarly to the embodiment shown in FIG. 5: the sealing element 1 has a sealing cap 41 that is surrounded by a safety cap 45. The height of the safety cap 45 is selected in such a way that it extends downward over sealing cap 41 far enough that a holding ring 79 can be provided on the lower edge of safety cap 45, this holding ring 77 engaging in a corresponding recess 81 that runs on the outer surface of the syringe body and thus anchoring the safety cap 45 on syringe body 77. A surrounding specified breakage point 69 is indicated by a gap in FIG. 9. If a force is exerted on safety cap 45, its upper part with sealing cap 41 breaks off. The lower edge remains on syringe body 77 with the holding ring 79.

Because of the specified breaking point 69, a sterilizing medium can get into the inside of safety cap 45 and sterilize both the outer surface of conical projection 53' and of holding ring 79. It is provided here that the safety cap 45 is manufactured completely of porous material in order to make the contact surface between sealing cap 41 and safety cap 45 accessible to the sterilizing medium. However, it would basically be adequate to provide channels or porous structures here in order to make the contact surface accessible. Ultimately it is also conceivable to provide projections and recesses here to form channels in the contact area between the two parts of sealing element in order to permit sterilization of the contact surface. This has already been explained with FIGS. 2 to 4 for another embodiment example. However, this basic principle can be transferred to the embodiment example shown in FIG. 9 with no problems.

Figure 9:
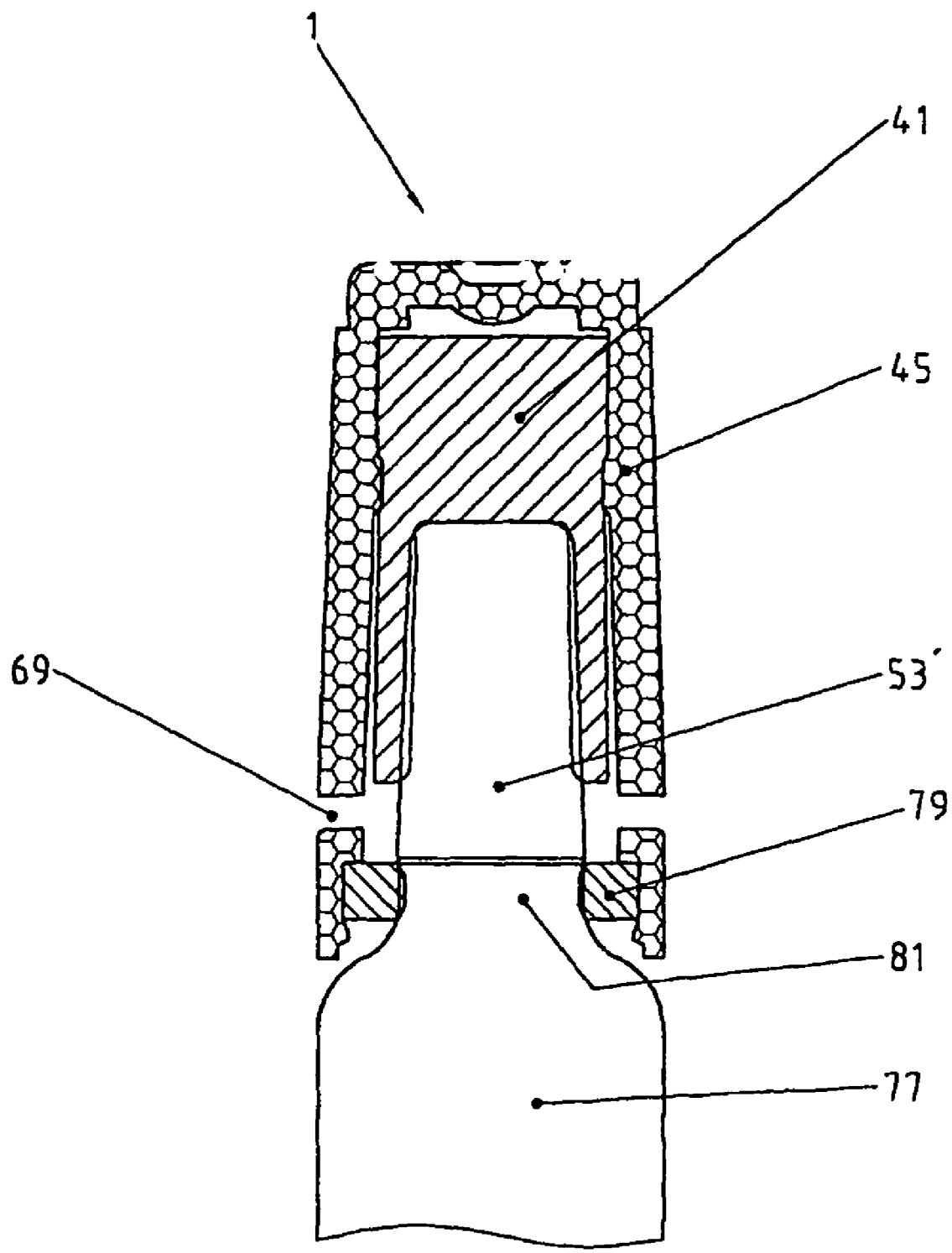
FIGS. 9 and 10 show a cross-section through other embodiments of the sealing element.

In turn, it can be seen from the diagram according to FIG. 9, that the safety cap 45 also serves for stabilizing the sealing cap 41 and presses this to seal it against the outer surface of the conical projection 53'. In this way, safety cap 45 also exhibits the function of a support element.

Figure 10:
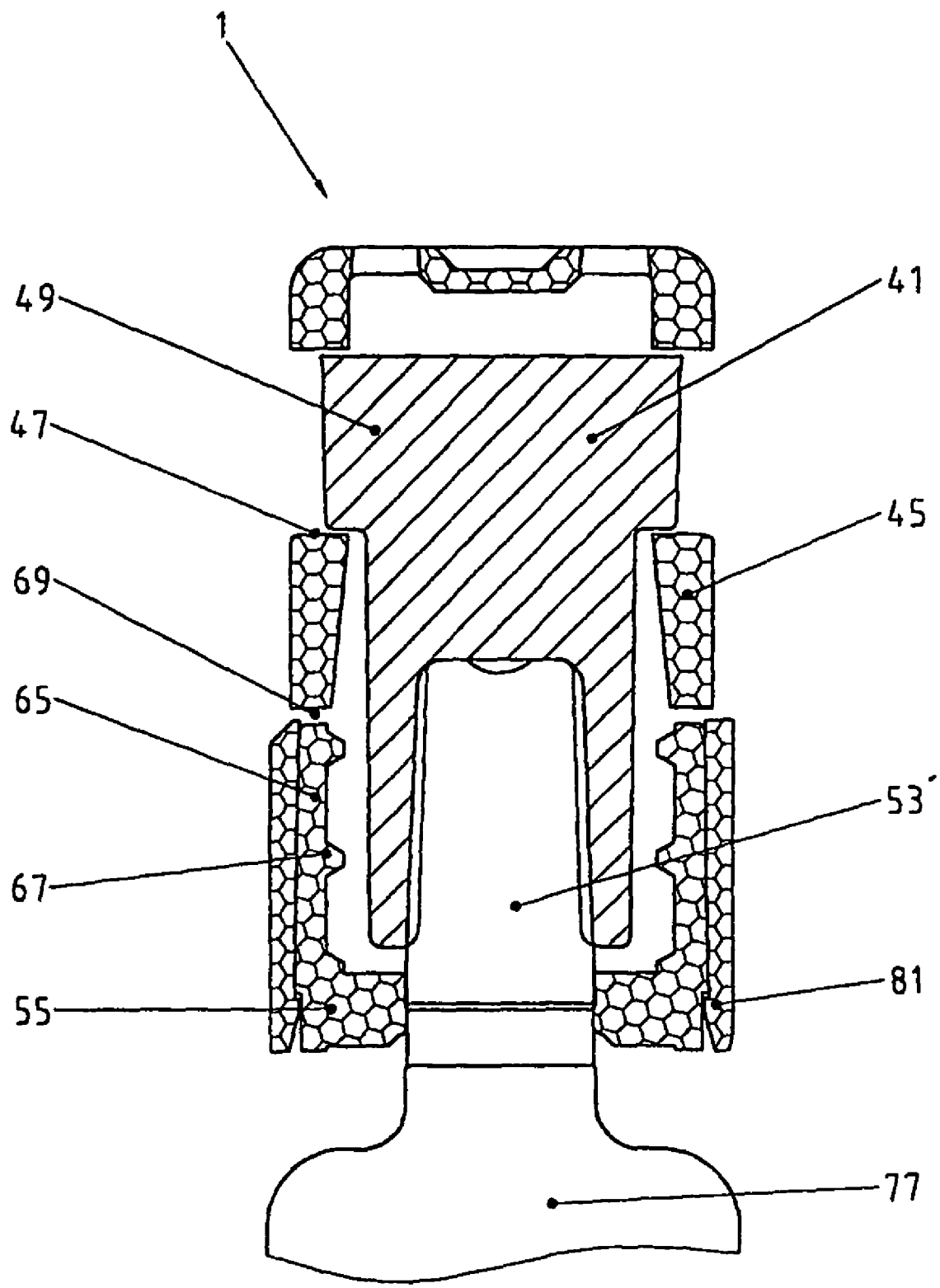

The cross-section drawing according to FIG. 10 shows a modified embodiment example of a sealing element 1. It has a sealing cap 41 that, as already described, can be mounted on the conical projection 53' of a syringe body 77. The sealing element also comprises a clamping element 55 that engages on the outside with syringe body 77 and/or in the lower area of the conical projection 53' and holds the sealing element 1. The clamping element 55 has a cylindrical projection 65 with an internal thread 67 that is used to securely hold a cannula mounted on the conical projection 53'.

On the outside, on clamping element 55 a safety cap 45 is mounted that engages on the outside of clamping element 55 with a sealing tab 81 and stresses the sealing cap 41. In the shroud surface of safety cap 45 there are recesses 47, into which the projections 49 of the sealing cap 41 engage. The recesses 47 serve, on one hand, as sight glasses and on the other, they offer contact shoulders for projections 49 so that the sealing cap 41, together with the safety cap 45, can be taken off the syringe body 77. A surrounding specified breaking point 69 is also indicated here by a gap, which is used to implement an original seal and leads to the fact that the upper part of the safety cap 45 breaks off if appropriately high forces are exerted. With the part of safety cap 45 that is broken off, the sealing cap 41 of sealing element 1 is then taken off the syringe body 77 so that the conical projection 53' is freely accessible.

In the embodiment example shown here, both the clamping element 55 and the safety cap 45 are manufactured of porous material, which ensures that the contact surfaces of the parts of sealing element 1 can securely be reached in a sterilizing procedure: on one hand, the contact area between safety cap 45 and clamping element 55 is safety sterilized and on the other, all contact surfaces between safety cap 45 and sealing cap 41 are sterilized.

Depending on the design of safety cap 45, this can also be used to stabilize the sealing cap 41. In this way, a support element can also be implemented for sealing element 1.

The following becomes clear from the explanations of FIGS. 1 to 10:

The sealing element is designed in such a way that contact areas and/or contact surfaces between the individual parts of the sealing element are accessible in a sterilizing procedure. This is possible in that an entire part provided with channels, porous structures, etc. is manufactured completely of a porous material. This was explained in more detail using the support element that is shown in FIG. 1. It is also conceivable that the contact areas between parts of the sealing element 1 can be provided with projections and/or recesses in order to form channels in the area of the contact surface, through which the sterilizing medium can flow. This was explained in detail with reference to FIGS. 3 to 4. The sealing element is thus characterized in that contact surfaces can be reached directly by sterilizing media. It is also conceivable that two parts, e.g., in this case a sealing cap 41 and a sealing stopper 61 do not contact each other directly, but contact a sterilizing element lying between them. In the embodiment examples shown here, the sterilization element was simultaneously designed as clamping element 55. It is also conceivable that in this case a stabilizing function is also taken over.

If a support element is provided in a sealing element, as was described with reference to FIGS. 1 to 4, the sealing element 1 can be used, in particular in connection with syringe systems in which the sealing element is provided with a suitable drive and stressed with pressure forces by way of a piston. The automatic systems are generally designed in such a way that if there are any irregularities, which in particular are based on undesirable elasticity of the sealing element, an automatic shutoff occurs. Because of the stabilizing of the sealing element by the support element, this type of malfunction can be prevented with a high degree of safety.

It has also been shown that with the use of a sterilization element, these different functions can be undertaken. It can serve as a clamping element for fastening the sealing element on a syringe body, but also to hold a cannula securely on a conical projection of the clamping element or on the conical projection of a syringe body.

In all cases, the sealing element has a simple design and because of this can be safely used in other areas of medicine, in that complete sterilizing of the given contact surfaces of parts of the sealing element is ensured.

The support element explained in FIGS. 1 to 4 is characterized by a significantly higher rigidity than is present in the sealing sleeve. However, in the other embodiment examples explained here, outstanding sterilization safety can be achieved, and in addition a very high stability of the sealing element, with the help of the sterilization element that is designed as a clamping element and/or as a safety cap.

In the following, the method for manufacturing a syringe system with a sealing element 1 will be discussed in more detail. At first, reference is made to FIGS. 2 to 4.

Sealing element 1 is manufactured in several procedural steps: first a support element 3 is brought into a first assembly position on the inside of a sealing sleeve 5. In this position, the support element 3 is fastened by a holding device that is created by ribs 21, 21' and 21''. The ribs hold the support element 3' at a distance from the inner surface of the sealing sleeve 5, so that a sterilization medium can be brought through the intermediate space into the inside of the sealing sleeve so that the later contact surfaces between the inner chamber of sealing sleeve 5 and the support element 3' can be sterilized.

After the sterilization, support element 3' is moved into its final position, which is shown in FIG. 4. In this position, it is fastened by the end areas of the ribs that serve as latching tabs.

The sterilization of the contact surface between two parts of a sealing element 1 can also be carried out with other embodiment examples.

Preferably the sterilization takes place in an autoclave that can also serve as a sluice, through which the sealing element is supplied to a filler device, in which a syringe can be filled with a medication and/or nutritional solution, etc. If necessary, the syringe can also be filled more after the sealing element is mounted, by moving it.

The invention claimed is:

1. A sealing element for sealing containers of medication, the sealing element comprising:
 a sealing member, the sealing member configured for engaging a package of medication so as to seal the package of medication so as to prevent fluid from entering or exiting the package of medication; and
 a permeable sterilization member, the sterilization member being disposed adjacent to the sealing member so as to be disposed outside of the package of medication where the sterilization member does not contact the medication and being formed from a porous material so as to be permeable to a sterilization fluid so as to allow the sterilization fluid to pass therethrough to sterilize the sealing member;
 wherein the sealing member comprises a cap placed over a container of medication to thereby seal the container of medication;
 wherein the sterilization member comprises a cap which is placed over the sealing member; and
 wherein the sterilization member comprises a clamping portion which attaches to the container of medication and a cap portion which attaches to the clamping portion.

2. A sealing element for sealing containers of medication, the sealing element comprising:
 a sealing member, the sealing member configured for engaging a package of medication so as to seal the package of medication; and
 a permeable sterilization member, the sterilization member being disposed adjacent to the sealing member and being formed from a porous material so as to be permeable to a sterilization fluid so as to allow the sterilization fluid to pass therethrough to sterilize the sealing member;
 and wherein the sterilization member further comprises channels formed therethrough.

3. A sealing element for sealing containers of medication, the sealing element comprising:

a sealing member, the sealing member configured for engaging a package of medication so as to seal the package of medication; and a permeable sterilization member, the sterilization member being disposed adjacent to the sealing member and being formed from a porous material so as to be permeable to a sterilization fluid so as to allow the sterilization fluid to pass therethrough to sterilize the sealing member; and wherein the sterilization member is designed as a clamping element and configured to clamp the sealing member in a position wherein the sealing member engages a package of medication to thereby close the package of medication.

4. The sealing element according to claim 3, wherein the sealing member comprises a sealing stopper and wherein the sealing element further comprises a sealing cap, and wherein the sterilization member has a first contact surface for engaging the sealing stopper and a second contact surface for engaging the sealing cap.

5. The sealing element according to claim 1, wherein the sterilization member has a conical projection configured for receiving a cannula.

6. The sealing element according to claim 4, wherein the first contact surface is disposed on the inside of the sterilization member and configured for engaging an outside surface of the sealing stopper, and wherein the second contact surface is disposed on the outside of the sterilization member and configured for engaging the inside of the sealing cap.

7. The sealing element according to claim 4, wherein the sealing stopper has a fluid channel therethrough that is closed by the sealing cap.

8. The sealing element according to claim 4, further comprising a safety cap, and wherein the safety cap is formed from a porous material so as to be permeable to sterilization fluid, and wherein the safety cap is disposed to cover the sealing cap.

9. The sealing element according to claim 8, wherein the safety cap comprises channels therethrough to permit the passage of sterilization fluid through the channels.

10. The sealing element according to claim 8, wherein the safety cap is attached to the sterilization member.

11. The sealing element of claim 1, wherein the sterilization member is attached to the container of medication independent of the sealing member.

12. The sealing element of claim 1, wherein the sterilization member comprises a breaking point whereby a portion of the sterilization member may be removed so as to expose the sealing member.

13. The sealing element of claim 1, wherein the sterilization member comprises openings formed therein, and wherein the sealing member comprises projections which engage the openings.

14. A sealing element for sealing containers of medication comprising:

a sealing member configured for engaging a container of medication so as to seal the container of medication; and a sterilization member configured for placement over the sealing member so as to generally cover the sealing member, the sterilization member being formed of a porous material, the material being permeable to fluid so as to allow a sterilization fluid to pass through the sterilization member to thereby sterilize the sealing member; and wherein the sealing member comprises a stopper configured for insertion into an opening in the container of medication, and wherein the sterilization member is configured for placement over the stopper and configured to engage the outside of the container of medication so as to hold the stopper in the container of medication.

15. The sealing element of claim 14, wherein the stopper has a channel therethrough, and wherein the device further comprises a cap for closing the channel.

16. The sealing element of claim 15, wherein the cap engages the sterilization member.

17. The sealing element of claim 14, wherein the sterilization member is permeable so as to allow sterilization fluid to pass therethrough.

18. A device for sealing containers of medication, the device comprising:

a sealing stopper configured for insertion into an opening in the container of medication; and a clamp element configured for placement over the stopper and configured to engage the outside of the container of medication so as to hold the stopper in the container of medication, the clamp element being formed from porous material, the material being permeable to fluid so as to allow sterilization fluid to pass therethrough to sterilize the sealing stopper.

19. The device of claim 18, wherein the sealing stopper has a central channel therethrough, and wherein the device further comprises a sealing cap which closes the central channel.

20. The device of claim 19, wherein the clamp element has a first contact surface for engaging the sealing stopper and a second contact surface for engaging the sealing cap.

21. The device of claim 20, wherein the first contact surface is disposed on the inside of the clamp element and configured for engaging an outside surface of the sealing stopper, and wherein the second contact surface is disposed on the outside of the clamp element and configured for engaging the inside of the sealing cap.

22. The device of claim 19, further comprising a safety cap disposed to cover the sealing cap.

23. The device of claim 22, wherein the safety cap locks onto the clamp element.

24. The device of claim 23, wherein the safety cap comprises an opening formed therethrough, the opening forming a breaking point so that an upper part of the safety cap may be broken off to expose the sealing cap.

25. The device of claim 22, wherein the safety cap is formed from a porous material.

* * * * *